(12) United States Patent
Huber et al.

(10) Patent No.: US 6,689,364 B2
(45) Date of Patent: Feb. 10, 2004

(54) BORRELIA BURGDORFERI POLYPEPTIDES AND USES THEREOF

(75) Inventors: Brigitte T. Huber, Cambridge, MA (US); Theresa Willett, Watertown, MA (US); Abbie Meyer, Roslindale, MA (US); Dawn Gross, Brighton, MA (US)

(73) Assignee: Tufts University, Boston, MA (US)

( * ) Notice: Subject to any disclaimer, the term of this patent is extended or adjusted under 35 U.S.C. 154(b) by 132 days.

(21) Appl. No.: 09/812,635

(22) Filed: Mar. 20, 2001

(65) Prior Publication Data

US 2002/0039586 A1 Apr. 4, 2002

Related U.S. Application Data

(60) Provisional application No. 60/190,949, filed on Mar. 21, 2000.

(51) Int. Cl.$^7$ .................. A61K 39/00; A61K 49/00; A61K 39/02; A61K 39/38
(52) U.S. Cl. .................. 424/190.1; 424/9.1; 424/9.2; 424/184.1; 424/185.1; 424/200.1; 424/234.1; 424/278.1; 530/300; 530/350; 536/23.1; 536/23.7
(58) Field of Search .................. 424/9.1, 9.2, 184.1, 424/185.1, 190.1, 200.1, 234.1, 278.1; 530/300, 350; 536/23.1, 23.7

(56) References Cited

U.S. PATENT DOCUMENTS 5,688,512 A   11/1997   Bergstrom et al. ....... 424/234.1

OTHER PUBLICATIONS

Gross, D.M. et al., *Science*, 281:703–706 (1998).
Gross, D.M. et al., *J. of Immunol.*, 160:1022–1028 (1998).
Steere, A.C. et al., *New Engl J. of Med.*, 339(4):209–215 (1998).
Sigal, L.H. et al., *New Engl. J. of Med.*, 339(4):216–222 (1998).
Akin, E., et al., *Infection and Immunity*, 69(3):1774–1780 (2001).
Fikrig, E. et al., *Proc. Natl. Acad. Sci. USA*, 89:5418–5421 (1992).
Fikrig, E. et al., *Science*, 250:553–556 (1990).
Kalish, R. et al., *Infection and Immunity*, 61(7):2774–2779 (1993).
Steere, A.C. et al., *Annals of Int. Med.*, 107(5):725–731 (1987).
Schaible, U.E. et al., *Proc. Natl. Acad. Sci. USA*, 87:3768–3772 (1990).
de Silva, A.M. et al., *J. Exp. Med.*, 183:271–275 (1996).
Kamradt, T. et al., *Infection and Immunity*, 64(4):1284–1289 (1996).
Steere, A.C. et al., *Annals of Int. Med.*, 90:896–901 (1979).
Barthold, S.W. et al., *Am. J. of Path.*, 143(3):959–971 (1993).
Steere, A.C. et al., *New Engl. J. of Med.*, 323(4):219–223 (1990).
Steere, A.C., *New Engl. J. Med.*, 345(2):115–125 (2001).

*Primary Examiner*—Rodney P Swartz
(74) *Attorney, Agent, or Firm*—Nixon Peabody LLP

(57) ABSTRACT

The present invention provides novel polypeptides which are substantially free of a *B. burgdorferi* spirochete or fragments thereof and which are thus useful in compositions and methods for the treatment and prevention of *B. burgdorferi* infection and Lyme disease. In one preferred embodiment, this invention provides modified OspA polypeptides and pharmaceutically effective compositions and methods comprising those polypeptides. Preferred modified OspA polypeptides are characterized by modifications which diminish and/or ablate their ability to bind the human MHC allele HLA-DRB1*0401.

3 Claims, 8 Drawing Sheets

| PROTEIN | SEQUENCE | *0401 BINDING PREDICTED SCORE |
|---|---|---|
| *B. burgdorferi* WT-OspA $_{165-173}$ | YVLEGTLTA | +6.5 |
| hLFA-1a $_{L332-340}$ | YVIEGTSKQ | +7.3 |
| *B. afzelii* OspA $_{165-173}$ | FTLEGKVAN | -1.3 |
| FTK-OspA $_{165-173}$ | FTLEGKLTA | +0.2 |

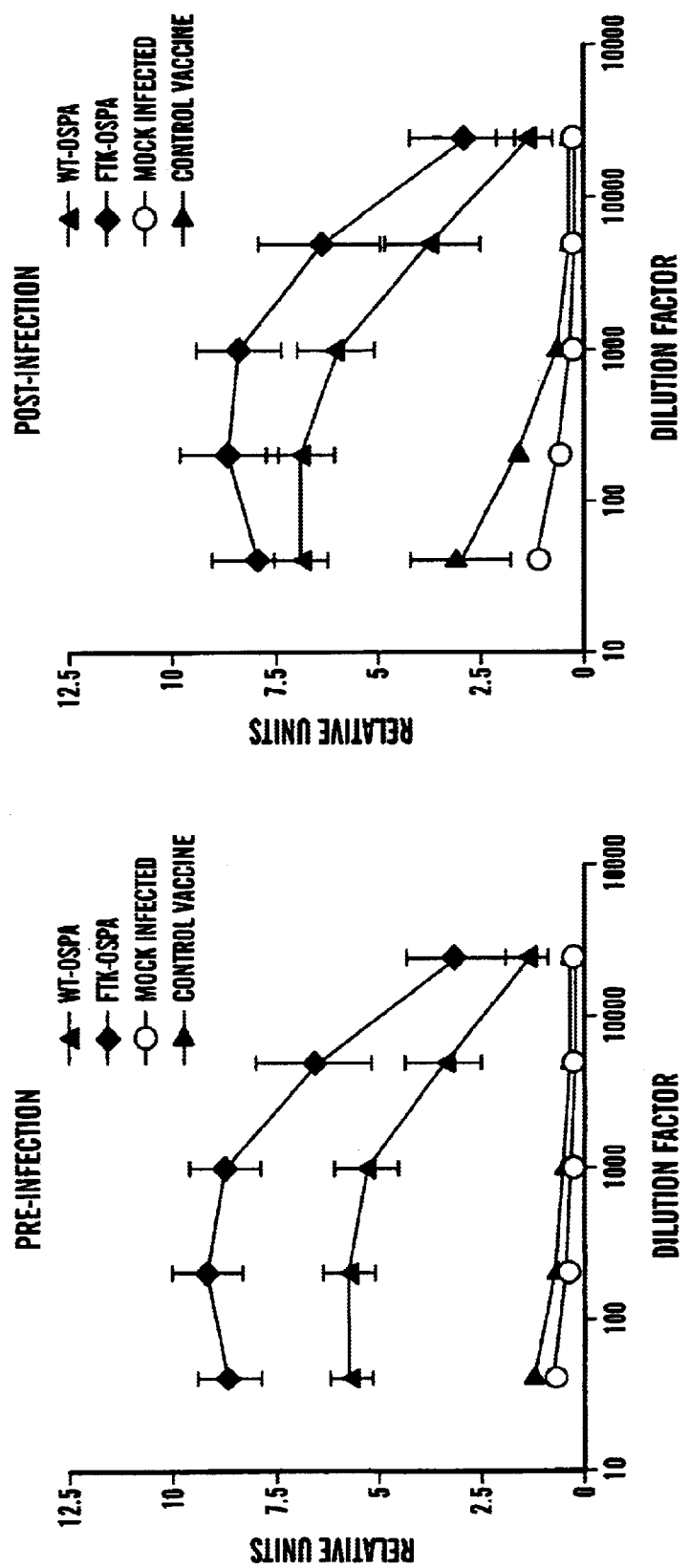

BORRELIA BURGDORFERI POLYPEPTIDES AND USES THEREOF

This application claims the benefit of Provisional Application No. 60/190,949 filed Nov. 21, 2000.

This invention was supported by National Institutes of Health Grant AR45386 and the government of the United States has certain rights thereto.

FIELD OF THE INVENTION

The present invention is directed to novel *Borrelia burgdorferi* polypeptides and uses thereof.

BACKGROUND OF THE INVENTION

Lyme borreliosis (Lyme disease) is the most common vector-borne infection in the United States [S. W. Barthold, et al., "An Animal Model For Lyme Arthritis", Ann. N.Y. Acad. Sci., 539, pp. 264–73 (1988)]. It has been reported in every continent except Antarctica. The clinical hallmark of Lyme Disease is an early expanding skin lesion known as erythema migrans, which may be followed weeks to months later by neurologic, cardiac, and joint abnormalities.

The causative agent of Lyme disease is a spirochete known as *Borrelia burgdorferi*, transmitted primarily by Ixodes ticks of the *Ixodes ricinus* complex. *B. burgdorferi* has also been shown to be carried in other species of ticks and in mosquitoes and deer flies, but it appears that only ticks of the *I. ricinus* complex are able to transmit the disease to humans.

Lyme disease generally occurs in three stages. Stage one involves localized skin lesions (erythema migrans) from which the spirochete is cultured more readily than at any other time during infection [B. W. Berger et al., "Isolation And Characterization Of The Lyme Disease Spirochete From The Skin Of Patients With Erythema Chronicum Migrans", J. Am. Acad. Dermatol., 3, pp. 444–49 (1985)]. Flu-like or meningitis-like symptoms are common at this time. Stage two occurs within days or weeks, and involves spread of the spirochete through the patient's blood or lymph to many different sites in the body including the brain and joints. Varied symptoms of this disseminated infection occur in the skin, nervous system, and musculoskeletal system, although they are typically intermittent. Stage three, or late infection, is defined as persistent infection, and can be severely disabling. Chronic arthritis, and syndromes of the central and peripheral nervous system appear during this stage, as a result of the ongoing infection and perhaps a resulting auto-immune disease [R. Martin et al., "Borrelia burgdorferi-Specific And Autoreactive T-Cell Lines From Cerebrospinal Fluid In Lyme Radiculomyelitis", Ann Neurol., 24, pp. 509–16 (1988); D. Gross et al., "Identification of LFA-1 as a Candidate Autoantigen in Treatment-Resistant Lyme Arthritis", Science 281, pp. 703–706 (1998)].

*B. burgdorferi* is much easier to culture from the tick than from humans, therefore at present, Lyme disease is diagnosed primarily by serology. The enzyme-linked immunosorbent assay (ELISA) is one method of detection, using sonicated whole spirochetes as the antigen [J. E. Craft et al., "The Antibody Response In Lyme Disease: Evaluation Of Diagnostic Tests", J. Infect. Dis., 149, pp. 789–95 (1984)]. However, false negative and, more commonly, false positive results are associated with currently available tests.

At present, all stages of Lyme disease are treated with antibiotics. Treatment of early disease is usually effective, however the cardiac, arthritic, and nervous system disorders associated with the later stages often do not respond to therapy [A. C. Steere, "Lyme Disease", New Eng. J. Med., 321, pp. 586–96 (1989)].

Like *Treponema pallidum*, which causes syphilis, and leptospirae, which cause an infectious jaundice, Borrelia belong to the eubacterial phylum of spirochetes [A. G. Barbour and S. F. Hayes, "Biology of Borrelia Species", Microbiol. Rev., 50, pp. 381–400 (1986)]. *Borrelia burgdorferi* have a protoplasmic cylinder that is surrounded by a cell membrane, then by flagella, and then by an outer membrane.

The *B. burgdorferi* outer surface proteins identified to date are believed to be lipoproteins, as demonstrated by labeling with [$^3$H]palmitate [M. E. Brandt et al., "Immunogenic Integral membrane Proteins of *Borrelia burgdorferi* Are Lipoproteins", Infect. Immun., 58, pp. 983–91 (1990)]. The two major outer surface proteins are the 31 kd outer-surface protein A (OspA) and the 34 kd outer surface protein B (OspB). Both proteins have been shown to vary from different isolates or from different passages of the same isolate as determined by their molecular weights and reactivity with monoclonal antibodies. OspC is a 22 kDa membrane lipoprotein previously identified as pC [R. Fuchs et al., "Molecular Analysis and Expression of a Borrelia burgdorferi Gene Encoding a 22 kDa Protein (pC) in Escherichia coli", Mol. Microbiol., 6, pp. 503–09 (1992)]. OspD is said to be preferentially expressed by low-passage, virulent strains of *B. burgdorferi* B31 [S. J. Norris et al., "Low-Passage-Associated Proteins of Borrelia burgdorferi B31: Characterization and Molecular Cloning of OspD, A Surfaced-Exposed, Plasmid-Encoded Lipoprotein", Infect. Immun., 60, pp. 4662–4672 (1992)].

Additional *B. burgdorferi* proteins identified to date include the 41 kD flagellin protein, which is known to contain regions of homology with other bacterial flagellins [G. S. Gassman et al., "Analysis of the Borrelia burgdorferi GeHo fla Gene and Antigenic Characterization of Its Gene Product", J. Bacteriol., 173, pp. 1452–59 (1991)] and a 93 kDa protein said to be localized to the periplasmic space [D. J. Volkman et al., "Characterization of an Immunoreactive 93 kDa Core Protein of Borrelia burgdorferi With a Human IgG Monoclonal Antibody", J. Immun., 146, pp. 3177–82 (1991)].

Recently, immunization of mice with recombinant OspA has been shown to be effective to confer long-lasting protection against subsequent infection with *B. burgdorferi* [E. Fikrig et al., "Long-Term Protection of Mice from Lyme Disease by Vaccination with OspA", Infec. Immun., 60, pp. 773–77 (1992)]. Protection by the OspA immunogens used to date appears to be somewhat strain specific, probably due to the heterogeneity of the OspA gene among different *B. burgdorferi* isolates. For example, immunization with OspA from *B. burgdorferi* strain N40 confers protection against subsequent infection with strains N40, B31 and CD 16, but not against strain 25015 [E. Fikrig et al., "Borrelia burgdorferi Strain 25015: Characterization of Outer Surface Protein A and Vaccination Against Infection", J. Immun., 148, pp. 2256–60 (1992)].

An additional problem with OspA as a protective immunogen is cross-reactivity at the T cell level observed between OspA$_{165-173}$ and LFA-1α. [D. Gross et al., "Identification of LFA-1 as a Candidate Autoantigen in Treatment-Resistant Lyme Arthritis", Science 281, pp. 703–706 (1998)]. As described above, a prominent late manifestation of infection with *B. burgdorferi* is Lyme arthritis[A. C. Steere, et al., Ann. Int. Med 90: 896 (1979); A. C. Steere, et al., Ann. Int.

Med. 107: 725 (1987); A. C. Steere, et al., *N. Eng. J. Med.* 321: 586 (1989); A. C. Steere, et al., *N. Eng. J. Med.* 323: 219 (1990); A. C. Steere, et al., *Arthritis Rheum.* 37: 878 (1994)]. About 10% of patients with Lyme arthritis develop a condition known as antibiotic-resistant Lyme arthritis, which typically affects one knee for months to years after multiple courses of antibiotics [A. C. Steere, et al., *Ann. Int. Med.* 90: 896 (1979); A. C. Steere, et al., *Ann. Int. Med.* 107: 725 (1987); A. C. Steere, et al., *N. Eng. J. Med.* 321: 586 (1989); A. C. Steere, et al., *Arthritis Rheum.* 37: 878 (1994)]. Such patients have no detectable spirochetal DNA in joint fluid after antibiotic therapy, which suggests that the spirochete has been eliminated by this treatment [J. F. Bradley, et al., *Ann. Int. Med.* 120: 487 (1994); J. J. Nocton et al., *N. Eng. J. Med.* 330: 229 (1994)]. The increased frequency of the HLA-DRB1*0401 allele in these patients suggests an autoimmune etiology [unpublished data] (Kalish et al., 1993 Infect Immun 61:2774–9).

Recent work has identified LFA-1α as a candidate autoantigen in treatment-resistant Lyme arthritis [D. Gross et al., "Identification of LFA-1 as a Candidate Autoantigen in Treatment-Resistant Lyme Arthritis", Science 281, pp. 703–706 (1998)]. The immunodominant epitope of OspA for T helper cells was identified, and a homology search revealed a peptide from human leukocyte function-associated antigen 1 (LFA-1α). Individuals with treatment-resistant Lyme arthritis, but not other forms of arthritis, generated responses to OspA, LFA-1α, and their highly related peptide epitopes. This finding indicates that the initial immune system response to infection with *B. burgdorferi* generates OspA-primed T cells which remain activated by stimulation with LFA-1α after the spirochete has been eliminated from the individual, leading to the release of inflammatory cytokines by these activated T cells and macrophages and resulting in tissue damage and joint destruction.

As prevention of tick infestation is imperfect, and Lyme disease may be missed or misdiagnosed when it does appear, there exists a continuing urgent need for an improved vaccine for the prevention of Lyme disease. Given the potential cross-reactivity between OspA and LFA-1a, the use of OspA as a protective immunogen in vaccines may be associated with the induction of an auto-immune reaction in certain populations, including individuals expressing the HLA-DRB1*0401 allele. Thus, it would be highly desirable to generate modified OspA polypeptides with diminished or no binding to the HLA-DRB1*0401 allele.

SUMMARY OF THE INVENTION

We have now discovered a modified OspA polypeptide which has diminished binding to HLA-DRB1*0401. The present invention provides a vaccine composition comprising an immunogenic amount of OspA, or a unique fragment of OspA, and a pharmaceutically acceptable carrier or vehicle, wherein said amount is sufficient to immunize a susceptible mammal against Lyme borreliosis, wherein said OspA has diminished binding to HLA-DRB1*0401.

A preferred embodiment of the invention provides a vaccine composition which includes the modified OspA polypeptide of SEQ ID NO:4, or any unique fragment of SEQ ID NO.:4.

Another embodiment of the invention provides a nucleotide sequence encoding a peptide as set forth in SEQ ID NO:4. The nucleotide sequence can further include a 5'-flanking region containing at least one promoter sequence for expression of the peptide.

Another embodiment of the invention provides a nucleotide sequence encodes a fusion polypeptide containing OspA, wherein said OspA has diminished binding to HLA-DRB1*0401 and comprises SEQ ID NO:4.

A further embodiment of invention provides a vector containing the isolated DNA molecule of SEQ ID NO:4.

A preferred method of the invention provides a method of protecting a susceptible mammal against Lyme borreliosis by administering an effective amount of a vaccine composition, in which the vaccine composition includes the modified OspA polypeptide of SEQ ID NO:4. Preferably, the vaccine composition is administered by subcutaneous or intramuscular administration. Even more preferably, the vaccine composition is administered orally.

The present invention also provides methods for producing a vaccine composition containing a substantially pure OspA polypeptide, by recovering the OspA polypeptide from a host organism transformed with a vector containing DNA encoding the OspA polypeptide, and admixing the OspA polypeptide with an immunologically acceptable carrier or vehicle.

Another embodiment of the invention provides a method for producing the vaccine composition by admixing the OspA polypeptide and the carrier or vehicle. Preferably, the method further includes adding an adjuvant.

BRIEF DESCRIPTION OF THE DRAWINGS

FIG. 1 shows the modification of the main OspA Tc epitope to minimize binding to HLA-DRB1*0401. The amino acid sequence of wildtype *B. burgdorferi* OspA$_{165-173}$ peptide (SEQ ID NO:1) is compared to the sequence of hLFA-1a$_{L332-340}$ peptide (SEQ ID NO:2) and *B. afzelii* OspA$_{165-173}$ peptide (SEQ ID NO:3). SEQ ID NO:4 is the amino acid sequence of FTK-OspA$_{165-173}$ peptide, designed to exhibit reduced binding to HLA-DRB1*0401.

FIG. 3A shows production of interferon-gamma; FIG. 3B shows production of interleukin 13.

FIG. 5A shows the results of trial A, in which mice were infected with 5×103 B. burgdorferi. FIG. 5B shows the results of trial B, in which mice were infected with 1×104 B. burgdorferi. 75% (12/16) of the mice vaccinated with wildtype OspA peptide prior to infection were protected from development of arthritis; 87.5% (14/16) of the mice vaccinated with FTK-OspA peptide prior to infection were protected. In contrast, none (0/11) of the "mock" group refers to mock-vaccination (PBS/CFA) and mock-infection (BSK with no Bb), so the mock group had no arthritis, as expected, on control-vaccinated mice were protected (i.e., they all developed arthritis).

FIGS. 7A and 7B shows serum OspA-specific IgG is similar for wildtype OspA and FTK-OspA immunized mice both pre-infection (FIG. 7A) and post-infection (FIG. 7B).

DISCLOSURE OF THE INVENTION

Figure 2:
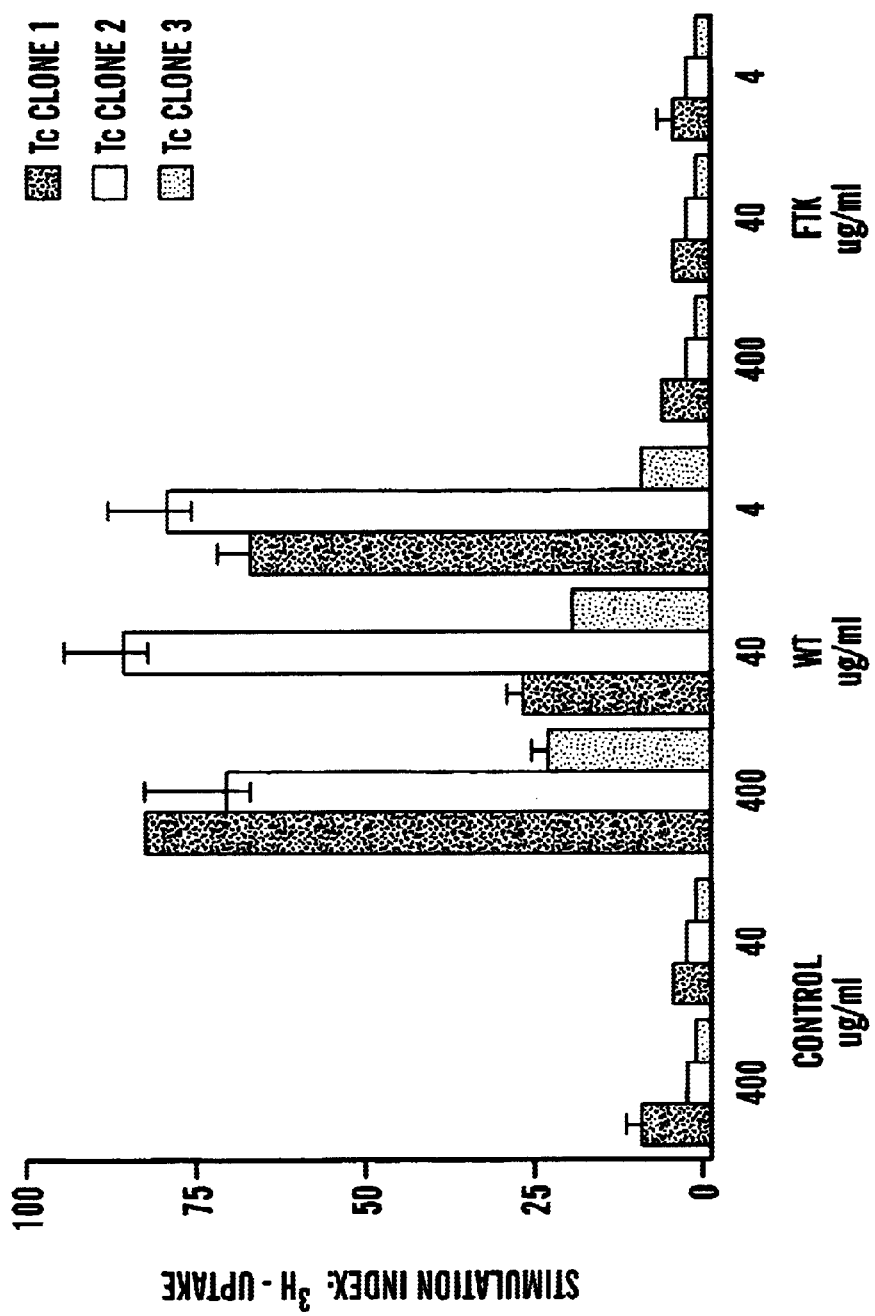
FIG. 2 shows the proliferation response of human DR4-restricted T cells clones to wildtype OspA and FTK-OspA peptides.

The present invention provides novel polypeptides which are substantially free of a B. burgdorferi spirochete or fragments thereof and which are thus useful in compositions and methods for the treatment and prevention of B. burgdorferi infection and Lyme disease. In one preferred embodiment, this invention provides modified OspA polypeptides and pharmaceutically effective compositions and methods comprising those polypeptides. A preferred modified OspA polypeptide is set forth in FIG. 1, below. Preferred modified OspA polypeptides are characterized by modifications which diminish and/or ablate their ability to bind the human MHC allele HLA-DRB1*0401.

The preferred compositions and methods of the invention are characterized by novel modified OspA polypeptides which elicit in treated animals the formation of an immune response, without causing the induction of an auto-immune reaction in certain populations, including individuals expressing the HLA-DRB1*0401 allele.

In another preferred embodiment, this invention provides a multicomponent vaccine comprising one or more novel modified OspA polypeptides of this invention in addition to one or more other immunogenic B. burgdorferi polypeptides. Such a vaccine is effective to confer broad protection against B. burgdorferi infection.

Finally, this invention provides DNA sequences that code for the novel modified polypeptides of this invention, recombinant DNA molecules that are characterized by those DNA sequences, unicellular hosts transformed with those DNA sequences and molecules, and methods of using those sequences, molecules and hosts to produce the novel polypeptides and multicomponent vaccines of this invention. DNA sequences of this invention are also advantageously used in a DNA vaccine for the prevention of Lyme disease and B. burgdorferi infection.

All of the novel B. burgdorferi polypeptides provided by this invention, and the DNA sequences encoding them, are substantially free of a B. burgdorferi spirochete or fragments thereof, and thus may be used in a variety of applications without the risk of unintentional infection or contamination with undesired B. burgdorferi components. Accordingly, the novel B. burgdorferi polypeptides of this invention are particularly advantageous in compositions and methods for the diagnosis and prevention of B. burgdorferi infection.

As used herein, an "immunogenic B. burgdorferi polypeptide" is any B. burgdorferi molecule that, when administered to an animal, is capable of eliciting an immune response that is effective to prevent or lessen the severity, for some period of time, of B. burgdorferi infection. Preventing or lessening the severity of infection may be evidenced by a change in the physiological manifestations of erythema migrans, arthritis, carditis, neurological disorders, and other Lyme disease related disorders. It may be evidenced by a decrease in or absence of spirochetes in the treated animal. And, it may be evidenced by a decrease in the level of spirochetes in infected ticks which have fed on treated animals.

The novel modified OspA polypeptides of the present invention have been modified to diminish and/or ablate their ability to bind the human MHC allele HLA-DRB1*0401, which in turn reduces the cross-reactivity associated with LFA-1 a and the induction of an auto-immune reaction in certain populations, including individuals expressing the HLA-DRB1*0401 allele. The present invention includes any modification of B. burgdorferi OspA which results in diminished binding to the HLA-DRB1*0401 allele.

Binding of OspA to HLA-DRB1*0401 is determined by measuring stimulation of T cells reactive with wildtype OspA. The stimulation of T cells is determined by measuring OspA-induced proliferation or cytokine production, including interferon gamma and interleukin 13 (see Examples, below).

Immunogenic B. burgdorferi polypeptides are intended to include not only the novel modified OspA polypeptides of this invention but also the Osp polypeptides disclosed in U.S. Pat. No. 5,656,451 and OspA and B polypeptides disclosed in PCT patent application WO 92/00055, as well as fragments, serotypic variants and derivatives of any of the above.

As used herein, a polypeptide which is "substantially free of a B. burgdorferi spirochete or fragments thereof" is a polypeptide that, when introduced into modified Barbour-Stoener-Kelly (BSK-II) medium and cultured at 37 degrees C. for 7 days, fails to produce any B. burgdorferi spirochetes detectable by dark field microscopy or a polypeptide that is detectable as a single band on an immunoblot probed with polyclonal anti-B. burgdorferi anti-serum.

As used herein, a "therapeutically effective amount" of a polypeptide is the amount that, when administered to an animal, elicits an immune response that is effective to prevent or lessen the severity, for some period of time, of B. burgdorferi infection.

The novel modified B. burgdorferi polypeptides disclosed herein are immunologically reactive with antisera generated by infection of a mammalian host with B. burgdorferi. Accordingly, they are useful in methods and compositions to diagnose and protect against Lyme disease, and in therapeutic compositions to stimulate immunological clearance of B. burgdorferi during ongoing infection. In addition, because the novel modified polypeptides disclosed herein are derived from OspA, an immunogenic surface protein of B. burgdorferi, they are particularly useful in a multicomponent vaccine against Lyme disease, because such a vaccine may be formulated to more closely resemble the immunogens presented by replication-competent B. burgdorferi, and because such a vaccine is more likely to confer broad-spectrum protection than a vaccine comprising only a single B. burgdorferi polypeptide. Multicomponent vaccines according to this invention may also contain polypeptides which characterize any currently existing or to be discovered vaccine useful for immunization of diseases other than Lyme disease such as, for example, diphtheria, polio, hepatitis, and measles. Such multicomponent vaccines are characterized by a single composition form.

The preferred compositions and methods of this invention comprise novel B. burgdorferi polypeptides having enhanced immunogenicity. Such polypeptides may result when the native forms of the polypeptides or fragments thereof are modified or subjected to treatments to enhance their immunogenic character in the intended recipient.

Numerous techniques are available and well known to those of skill in the art which may be used, without undue experimentation, to substantially increase the immunogenicity of the novel B. burgdorferi polypeptides herein disclosed. For example, the polypeptides may be modified by coupling to dinitrophenol groups or arsanilic acid, or by denaturation with heat and/or SDS. Particularly if the polypeptides are small polypeptides synthesized chemically, it may be desirable to couple them to an immunogenic carrier. The coupling of course, must not interfere with the ability of either the polypeptide or the carrier to function appropriately. For a review of some general considerations in coupling strategies, see Antibodies, A Laboratory Manual, Cold Spring Harbor Laboratory, ed. E. Harlow and D. Lane (1988). Useful immunogenic carriers are well known in the art. Examples of such carriers are keyhole limpet hemocyanin (KLH); albumins such as bovine serum albumin (BSA) and ovalbumin, PPD (purified protein derivative of tuberculin); red blood cells; tetanus toxoid; cholera toxoid; agarose beads; activated carbon; or bentonite.

Modification of the amino acid sequence of the novel *B. burgdorferi* polypeptides disclosed herein in order to alter the lipidation state is also a method which may be used to increase their immunogenicity and biochemical properties. For example, the polypeptides or fragments thereof may be expressed with or without the signal sequences that direct addition of lipid moieties.

As will be apparent from the disclosure to follow, the polypeptides may also be prepared with the objective of increasing stability or rendering the molecules more amenable to purification and preparation. One such technique is to express the polypeptides as fusion proteins comprising other *B. burgdorferi* or non-*B. burgdorferi* sequences.

In accordance with this invention, derivatives of the novel *B. burgdorferi* polypeptides may be prepared by a variety of methods, including by in vitro manipulation of the DNA encoding the native polypeptides and subsequent expression of the modified DNA, by chemical synthesis of derivatized DNA sequences, or by chemical or biological manipulation of expressed amino acid sequences.

OspA DNA may be obtained using the method of Lobet et al., U.S. Pat. No. 5,942,236, which is hereby incorporated by reference.

For example, derivatives may be produced by substitution of one or more amino acids with a different natural amino acid, an amino acid derivative or non-native amino acid, conservative substitution being preferred, e.g., 3-methylhistidine may be substituted for histidine, 4-hydroxyproline may be substituted for proline, 5-hydroxylysine may be substituted for lysine, and the like.

Causing amino acid substitutions which are less conservative may also result in desired derivatives, e.g., by causing changes in charge, conformation and other biological properties. Such substitutions would include for example, substitution of a hydrophilic residue for a hydrophobic residue, substitution of a cysteine or proline for another residue, substitution of a residue having a small side chain for a residue having a bulky side chain or substitution of a residue having a net positive charge for a residue having a net negative charge. When the result of a given substitution cannot be predicted with certainty, the derivatives may be readily assayed according to the methods disclosed herein to determine the presence or absence of the desired characteristics.

In another embodiment of this invention, the novel *B. burgdorferi* polypeptides disclosed herein may be prepared as part of a larger fusion protein. For example, a novel *B. burgdorferi* polypeptide of this invention may be fused at its N-terminus or C-terminus to a different immunogenic *B. burgdorferi* polypeptide, to a non-*B. burgdorferi* polypeptide or to combinations thereof, to produce fusion proteins comprising the novel *B. burgdorferi* polypeptide.

In a preferred embodiment of this invention, fusion proteins comprising novel *B. burgdorferi* polypeptides are constructed comprising B cell and/or T cell epitopes from multiple serotypic variants of *B. burgdorferi*, each variant differing from another with respect to the locations or sequences of the epitopes within the polypeptide. In a more preferred embodiment, fusion proteins are constructed which comprise one or more of the novel *B. burgdorferi* polypeptides fused to other immunogenic *B. burgdorferi* polypeptides. Such fusion proteins are particularly effective in the prevention, treatment and diagnosis of Lyme disease as caused by a wide spectrum of *B. burgdorferi* isolates.

In another embodiment of this invention, the novel *B. burgdorferi* polypeptides may be fused to moieties, such as immunoglobulin domains, which may increase the stability and prolong the in vivo plasma half-life of the polypeptide. Such fusions may be prepared according to methods well known to those of skill in the art, for example, in accordance with the teachings of U.S. Pat. Nos. 4,946,778, or 5,116,964. The exact site of the fusion is not critical as long as the polypeptide retains the desired biological activity. Such determinations may be made according to the teachings herein or by other methods known to those of skill in the art.

It is preferred that the fusion proteins comprising the novel *B. burgdorferi* polypeptides be produced at the DNA level, e.g., by constructing a nucleic acid molecule encoding the fusion, transforming host cells with the molecule, inducing the cells to express the fusion protein, and recovering the fusion protein from the cell culture. Alternatively, the fusion proteins may be produced after gene expression according to known methods.

The novel *B. burgdorferi* polypeptides may also be part of larger multimeric molecules which may be produced recombinantly or may be synthesized chemically. Such multimers may also include the polypeptides fused or coupled to moieties other than amino acids, including lipids and carbohydrates.

Preferably, the multimeric proteins will consist of multiple T or B cell epitopes or combinations thereof repeated within the same molecule, either randomly, or with spacers (amino acid or otherwise) between them.

In the most preferred embodiment of this invention, the novel modified *B. burgdorferi* polypeptides of this invention which are also immunogenic *B. burgdorferi* polypeptides are incorporated into a multicomponent vaccine which also comprises other immunogenic *B. burgdorferi* polypeptides. Such a multicomponent vaccine, by virtue of its ability to elicit antibodies to a variety of immunogenic *B. burgdorferi* polypeptides, will be effective to protect against Lyme disease as caused by a broad spectrum of different *B. burgdorferi* isolates, even those that may not express one or more of the Osp proteins.

The multicomponent vaccine may contain the novel *B. burgdorferi* polypeptides as part of a multimeric molecule in which the various components are covalently associated. Alternatively, it may contain multiple individual components. For example, a multicomponent vaccine may be prepared comprising two or more of the novel *B. burgdorferi* polypeptides, or comprising one novel *B. burgdorferi* polypeptide and one previously identified *B. burgdorferi* polypeptide, wherein each polypeptide is expressed and purified from independent cell cultures and the polypeptides are combined prior to or during formulation.

Alternatively, a multicomponent vaccine may be prepared from heterodimers or tetramers wherein the polypeptides have been fused to immunoglobulin chains or portions thereof. Such a vaccine could comprise, for example, a novel polypeptide fused to an immunoglobulin heavy chain and an OspB polypeptide fused to an immunoglobulin light chain, and could be produced by transforming a host cell with DNA encoding the heavy chain fusion and DNA encoding the light chain fusion. One of skill in the art will understand that the host cell selected should be capable of assembling the two chains appropriately. Alternatively, the heavy and light chain fusions could be produced from separate cell lines and allowed to associate after purification.

The desirability of including a particular component and the relative proportions of each component may be determined by using the assay systems disclosed herein, or by using other systems known to those in the art. Most preferably, the multicomponent vaccine will comprise numerous T cell and B cell epitopes of immunogenic B. burgdorferi polypeptides, including the novel B. burgdorferi polypeptides of this invention.

This invention also contemplates that the novel B. burgdorferi polypeptides of this invention, either alone or with other immunogenic B. burgdorferi polypeptides, may be administered to an animal via a liposome delivery system in order to enhance their stability and/or immunogenicity. Delivery of the novel B. burgdorferi polypeptides via liposomes may be particularly advantageous because the liposome may be internalized by phagocytic cells in the treated animal. Such cells, upon ingesting the liposome, would digest the liposomal membrane and subsequently present the polypeptides to the immune system in conjunction with other molecules required to elicit a strong immune response.

The liposome system may be any variety of unilamellar vesicles, multilamellar vesicles, or stable plurilamellar vesicles, and may be prepared and administered according to methods well known to those of skill in the art, for example in accordance with the teachings of U.S. Pat. Nos. 5,169,637, 4,762,915, 5,000,958 or 5,185,154. In addition, it may be desirable to express the novel B. burgdorferi polypeptides of this invention, as well as other selected B. burgdorferi polypeptides, as lipoproteins, in order to enhance their binding to liposomes.

Any of the novel B. burgdorferi polypeptides of this invention may be used in the form of a pharmaceutically acceptable salt. Suitable acids and bases which are capable of forming salts with the polypeptides of the present invention are well known to those of skill in the art, and include inorganic and organic acids and bases.

According to this invention, we describe a method which comprises the steps of treating an animal with a therapeutically effective amount of a novel B. burgdorferi polypeptide, or a fusion protein or a multimeric protein comprising a novel B. burgdorferi polypeptide, in a manner sufficient to prevent or lessen the severity, for some period of time, of B. burgdorferi infection. The polypeptides that are preferred for use in such methods are those that contain protective epitopes. Such protective epitopes may be B cell epitopes, T cell epitopes, or combinations thereof.

According to another embodiment of this invention, we describe a method which comprises the steps of treating an animal with a multicomponent vaccine comprising a therapeutically effective amount of a novel B. burgdorferi polypeptide, or a fusion protein or multimeric protein comprising such polypeptide in a manner sufficient to prevent or lessen the severity, for some period of time, of B. burgdorferi infection. Again, the polypeptides, fusion proteins and multimeric proteins that are preferred for use in such methods are those that contain protective epitopes, which may be B cell epitopes, T cell epitopes, or combinations thereof. One of skill in the art will also understand that it may be advantageous to administer the novel B. burgdorferi polypeptides of this invention in a form that will favor the production of T-helper cells type 2 (TH 2), which help B cells to generate antibody responses. Aside from administering epitopes which are strong B cell epitopes, the induction of TH 2 cells may also be favored by the mode of administration of the polypeptide for example by administering in certain doses or with particular adjuvants and immunomodulators, for example with interleukin-4.

To prepare the preferred polypeptides of this invention, in one embodiment, overlapping fragments of the novel B. burgdorferi polypeptides of this invention are constructed. The polypeptides that contain B cell epitopes may be identified in a variety of ways for example by their ability to (1) remove protective antibodies from polyclonal antiserum directed against the polypeptide or (2) elicit an immune response which is effective to prevent or lessen the severity of B. burgdorferi infection.

The DNA sequences encoding the polypeptides of this invention may or may not encode a signal sequence. If the expression host is eukaryotic, it generally is preferred that a signal sequence be encoded so that the mature protein is secreted from the eukaryotic host.

An amino terminal methionine may or may not be present on the expressed polypeptides of this invention. If the terminal methionine is not cleaved by the expression host, it may, if desired, be chemically removed by standard techniques.

A wide variety of expression host/vector combinations may be employed in expressing the DNA sequences of this invention. Useful expression vectors for eukaryotic hosts, include, for example, vectors comprising expression control sequences from SV40, bovine papilloma virus, adenovirus, adeno-associated virus, cytomegalovirus and retroviruses. Useful expression vectors for bacterial hosts include bacterial plasmids, such as those from E. coli, including pBluescript, pGEX-2T, pUC vectors, col E1, pCR1, pBR322, pMB9 and their derivatives, wider host range plasmids, such as RP4, phage DNAs, e.g., the numerous derivatives of phage lambda, e.g. .lambda.GT10 and .lambda.GT11, and other phages. Useful expression vectors for yeast cells include the 2 micron. plasmid and derivatives thereof. Useful vectors for insect cells include pVL 941.

In addition, any of a wide variety of expression control sequences—sequences that control the expression of a DNA sequence when operatively linked to it—may be used in these vectors to express the DNA sequences of this invention. Such useful expression control sequences include the expression control sequences associated with structural genes of the foregoing expression vectors. Examples of useful expression control sequences include, for example, the early and late promoters of SV40 or adenovirus, the lac system, the trp system, the TAC or TRC system, the T3 and T7 promoters, the major operator and promoter regions of phage lambda, the control regions of fd coat protein, the promoter for 3-phosphoglycerate kinase or other glycolytic enzymes, the promoters of acid phosphatase, e.g., Pho5, the promoters of the yeast .alpha.-mating system and other constitutive and inducible promoter sequences known to control the expression of genes of prokaryotic or eukaryotic cells or their viruses, and various combinations thereof.

In a preferred embodiment, DNA sequences encoding the novel B. burgdorferi polypeptides of this invention are cloned in the expression vector lambda ZAP II (Stratagene, La Jolla, Calif.), in which expression from the lac promoter may be induced by IPTG.

In another preferred embodiment, DNA encoding the novel B. burgdorferi polypeptides of this invention is inserted in frame into an expression vector that allows high level expression of the polypeptide as a glutathione S-transferase fusion protein. Such a fusion protein thus contains amino acids encoded by the vector sequences as well as amino acids of the novel *B. burgdorferi* polypeptide.

A wide variety of unicellular host cells are useful in expressing the DNA sequences of this invention. These hosts may include well known eukaryotic and prokaryotic hosts, such as strains of *E. coli*, Pseudomonas, Bacillus, Streptomyces, fungi, yeast, insect cells such as Spodoptera frugiperda (SF9), animal cells such as CHO and mouse cells, African green monkey cells such as COS 1, COS 7, BSC 1, BSC 40, and BMT 10, and human cells, as well as plant cells in tissue culture.

It should of course be understood that not all vectors and expression control sequences will function equally well to express the DNA sequences of this invention. Neither will all hosts function equally well with the same expression system. However, one of skill in the art may make a selection among these vectors, expression control sequences and hosts without undue experimentation and without departing from the scope of this invention. For example, in selecting a vector, the host must be considered because the vector must be replicated in it. The vector's copy number, the ability to control that copy number, the ability to control integration, if any, and the expression of any other proteins encoded by the vector, such as antibiotic or other selection markers, should also be considered.

In selecting an expression control sequence, a variety of factors should also be considered. These include, for example, the relative strength of the sequence, its controllability, and its compatibility with the DNA sequence of this invention, particularly with regard to potential secondary structures. Unicellular hosts should be selected by consideration of their compatibility with the chosen vector, the toxicity of the product coded for by the DNA sequences of this invention, their secretion characteristics, their ability to fold the polypeptide correctly, their fermentation or culture requirements, and the ease of purification from them of the products coded for by the DNA sequences of this invention.

Within these parameters, one of skill in the art may select various vector/expression control sequence/host combinations that will express the DNA sequences of this invention on fermentation or in other large scale cultures.

The molecules comprising the novel *B. burgdorferi* polypeptides encoded by the DNA sequences of this invention may be isolated from the fermentation or cell culture and purified using any of a variety of conventional methods including: liquid chromatography such as normal or reversed phase, using HPLC, FPLC and the like; affinity chromatography (such as with inorganic ligands or monoclonal antibodies); size exclusion chromatography; immobilized metal chelate chromatography; gel electrophoresis; and the like. One of skill in the art may select the most appropriate isolation and purification techniques without departing from the scope of this invention.

In addition, the novel *B. burgdorferi* polypeptides may be generated by any of several chemical techniques. For example, they may be prepared using the solid-phase synthetic technique originally described by R. B. Merrifield, "Solid Phase Peptide Synthesis. I. The Synthesis Of A Tetrapeptide", J. Am. Chem. Soc., 83, pp. 2149–54 (1963), or they may be prepared by synthesis in solution. A summary of peptide synthesis techniques may be found in E. Gross & H. J. Meinhofer, 4 The Peptides: Analysis, Synthesis, Biology; Modern Techniques Of Peptide And Amino Acid Analysis, John Wiley & Sons, (1981) and M. Bodanszky, Principles Of Peptide Synthesis, Springer-Verlag (1984).

Typically, these synthetic methods comprise the sequential addition of one or more amino acid residues to a growing peptide chain. Often peptide coupling agents are used to facilitate this reaction. For a recitation of peptide coupling agents suitable for the uses described herein see M. Bodansky, supra. Normally, either the amino or carboxyl group of the first amino acid residue is protected by a suitable, selectively removable protecting group. A different protecting group is utilized for amino acids containing a reactive side group, e.g., lysine. A variety of protecting groups known in the field of peptide synthesis and recognized by conventional abbreviations therein, may be found in T. Greene, Protective Groups In Organic Synthesis, Academic Press (1981).

EXAMPLE

Methods

Modification of the T-cell epitope in OspA was carried out using a PCR-based site-directed mutagenesis. The 3 amino acid substitutions were made using mutated PCR-primers to amplify a new DNA template incorporating the modifications. The resulting modified DNA sequence was then cloned into a protein-expression vector, pGEX4T.1, which contains an N-terminal GST tag. The tag was used to purify the protein on an affinity column, then the tag was cleaved with thrombin protease, releasing the recombinant OspA from the column. The expression vector without any OspA coding sequence was treated identically to the WT and FTK-containing vectors to produce the Control vaccine, which contained any background bacterial proteins that might have an affect on the experimental outcome. The modifications were designed to minimize predicted binding to HLA-DRB1*0401 based on the algorithm published by Hammer et al (Hammer J, Bono E, Gallazzi F, Belunis C, Nagy Z, Sinigaglia F. (1994) Precise Prediction of Major Histocompatibility Complex Class II-Peptide Interaction Based on Peptide Side Chain Scanning. J Exp Med. 180:2353–2358) The FTK substitutions were also made keeping the sequence of the a European isolate of Bb, B afzelii, as a template to increase the likelihood that the resulting protein would be unchanged structurally.

Human T cells were cloned from the synovial fluid of an HLA DRB1*0401 homozygous patient based upon their ability to recognize the epitope OspA165–173 in the context of HLA-DRB1*0401. These clones were then tested for their ability to respond functionally to wild type versus FTK OspA by either proliferation or cytokine secretion. The responses of the clones to FTK-OspA was similar to the control responses, indicating that our modifications altered the OspA165–173 epitope sufficiently to block T cell recognition of it.

The mouse vaccination protocol was based upon experiments in the literature which initially identified OspA as having potential as a vaccine. The vaccine has not been tested in vivo with tick challenge due to the technically difficult nature of the animal handling for such experiments. However, the artificial system used here has been utilized by others in the past and reflects accurately on the protective ability of the modified vaccine. (Fikrig et al, 1997 Immunity 6:531–539; Bockenstedt et al,1993 J Immunol 151:900–906, Fikrig et al, 1992 PNAS 89:5418–5421)

Acute arthritis was used to represent infection, as all mice that were shown to have Bb present in their blood or bladders were shown to have arthritis. The correlation between infection and arthritis, measured for the first vaccination trial, was 1:1.

The mAb LA-2 has been considered the "gold-standard" in terms of OspA-specific antibody responses which are protective, as it has been shown that if animals do not make a response to the epitope recognized by LA-2, they will not be protected by OspA vaccination (Johnson B et al, 1995 Vaccine 13(12): 1086–1094).

Results

The novel modified OspA polypeptide, referred to herein as FTK-OspA, of the present invention has been modified to diminish and/or ablate the ability to bind the human MHC allele HLA-DRB1*0401, which in turn reduces the potential cross-reactivity associated with LFA-1 a and the induction of an auto-immune reaction in certain populations, including individuals expressing the HLA-DRB1*0401 allele.

The novel OspA polypeptide, FTK-OspA, of the present invention was modified within a nine amino acid stretch, representing amino acids 165–173, the epitope that binds to HLA-DRB1*0401(see FIG. 1) [D. Gross et al., Science 281, 703–706 (1998)].

The FTK-OspA peptide (SEQ ID NO:4), corresponding to OspA165–173, was designed to exhibit diminished binding to HLA-DRB1*0401. The basis for modifying this cross-reacting epitope was comparison to the related species of Borrelia, B. afzelli. This species is found throughout Europe and, similar to B. burgdorferi, also causes Lyme disease. However, unlike B. burgdorferi, this species is not strongly associated with treatment-resistant Lyme arthritis, indicating that it lacks the cross-reacting epitope at OspA165–173.

Analysis of the OspA165–173 peptide sequence indicated that the B. afzelli peptide has diminished binding of HLA-DRB1*0401 relative to B. burgdorferi OspA (see FIG. 1). A HLA-DRB1*0401 peptide-binding algorithm was used to predict the binding of each peptide [J. Hammer et al., J. Exp. Med. 180: 2353 (1994); K. W. Marshall et al., J. Immunol. 15 (1995)]. According to this algorithm, only peptides with scores greater than 2 are likely to bind and be able to be presented by the HLA-DRB1*0401 molecule. As shown in FIG. 1, B. burgdorferi has a binding score of 6.5 in the HLA-DRB1*0401 peptide-binding algorithm, and the cross-reacting autoantigen hLFA-1aL332–340 has a binding score of 7.3. In contrast, the B. afzelli peptide has a binding score of −1.3.

To design a OspA polypeptide with reduced ability to bind the human MHC allele HLA-DRB1*0401, the sequence of the OspA165–173 peptide was modified to resemble the corresponding sequence in the B. afzelli peptide (see FIG. 1). In this modified peptide, designated the FTK-OspA mutant, the following amino acid substitutions were made: tyrosine 165 was changed to phenylalanine; valine 166 was changed to threonine; and threonine 170 was changed to lysine. The HLA-DRB1*0401 peptide-binding algorithm predicts a binding score of 0.2 for the FTK-OspA mutant.

Figures 3A, 3B:
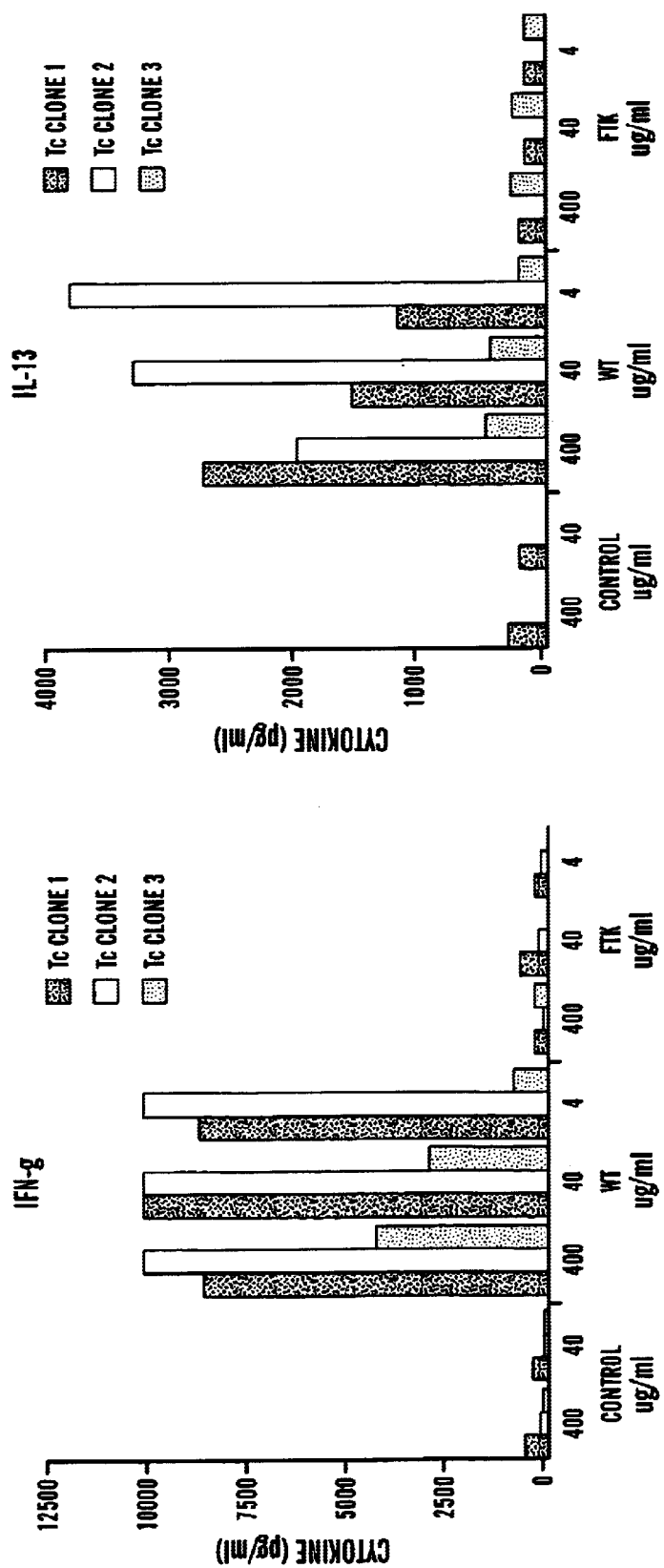
FIGS. 3A and 3B show cytokine production by T cell clones in response to stimulation by wildtype OspA and FTK-OspA peptides.

The full length modified OspA polypeptide bearing the FTK-OspA mutant sequence at amino acids 165–173 was analyzed further. The modified polypeptide was comparable to wildtype OspA in binding to the protective anti-OspA monoclonal antibody CIII.78, as measured in competitive ELISA assays. However, in vitro analyses confirmed that the mutant has significantly decreased ability to stimulate HLA-DRB1*0401 restricted OspA-specific human T cell clones. Three different human DR4-restricted T cell clones from a patient with treatment-resistant Lyme arthritis were selected for their ability to respond to the wild type OSpA165–173 peptide. In FIG. 2, the proliferation response of the T cells clones to wildtype OspA and FTK-OspA peptides is shown. These T cells proliferate in response to stimulation with wildtype OspA, but not FTK-OspA. Similarly, in FIG. 3 it is shown that stimulation of these T cell clones with wildtype OspA peptide induces production of the cytokines interferon gamma and interleukin 13, but not in response to stimulation with the modified FTK-OspA peptide.

Figure 4:
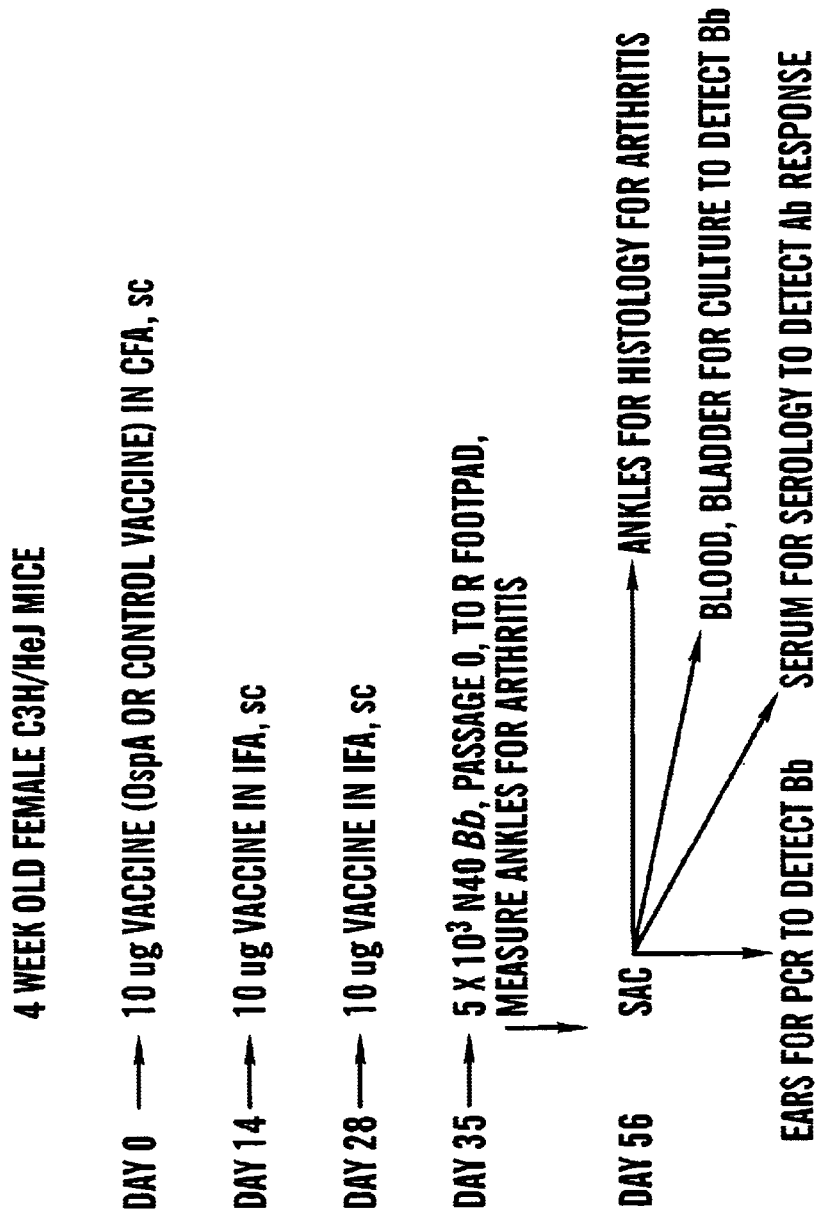
FIG. 4 shows the vaccination protocol used to deliver wildtype OspA and FTK-OspA peptides to mice.

To determine whether the FTK-OspA could protect against development of Lyme arthritis, mice were vaccinated and then challenged with infection by *B. burgdorferi* (FIG. 4). Mice were vaccinated with 10 μg of wildtype OspA, FTK-OspA, or control vaccine on days 0, 14, and 28. On day 35, the vaccinated mice were exposed to 5×10$^3$ or 1×10$^4$ passage 0 N40 *B. burgdorferi* in the right footpad. On day 56, mice were sacrificed and the following tissue samples were taken for further analysis: ankles (for histology to analyze arthritis), blood and bladder (for culture to detect *B. burgdorferi*), serum (for serology to determine the antibody response), and ears (for PCR to detect *B. burgdorferi*).

Figure 5A:
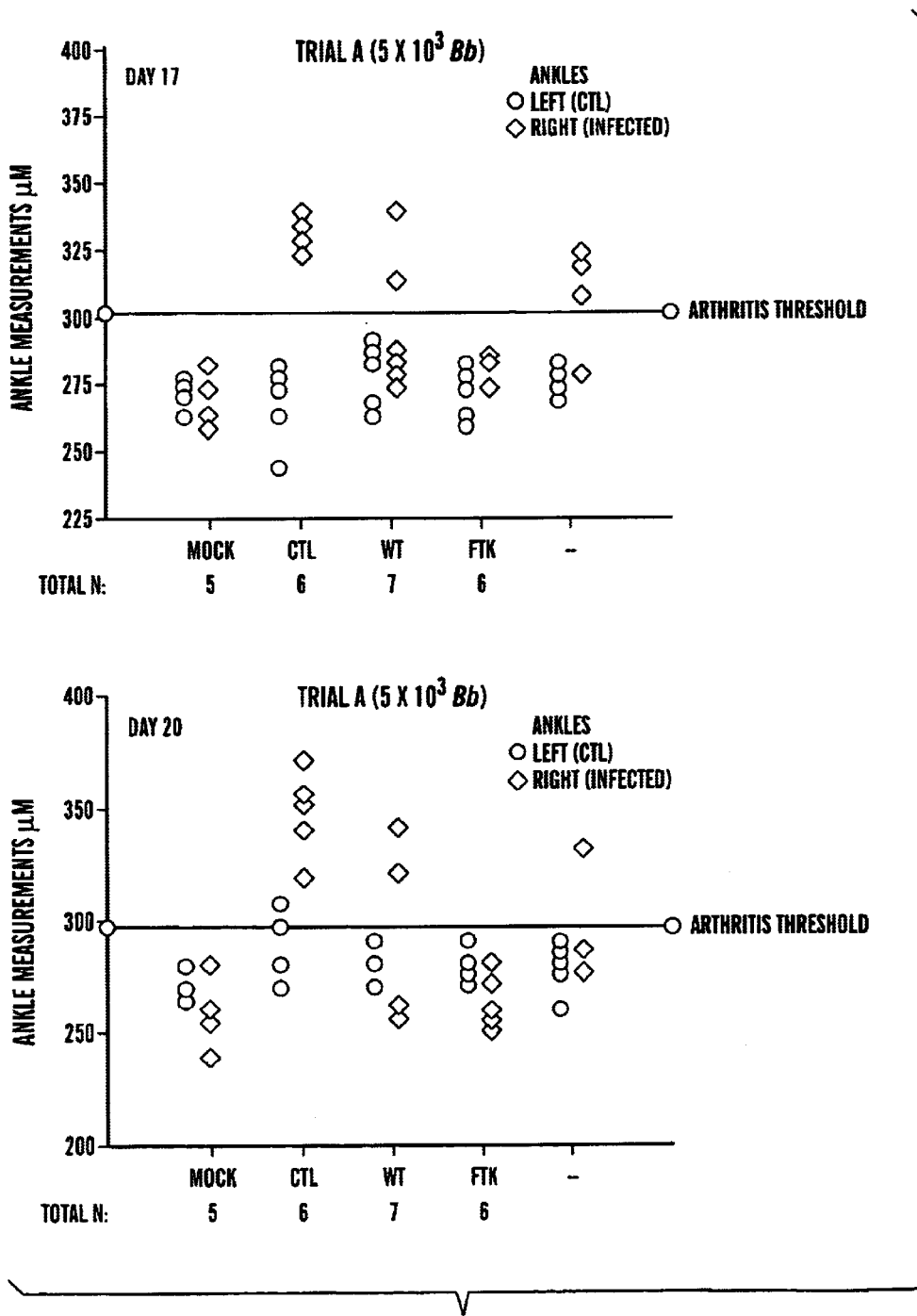
FIGS. 5A and 5B show that wildtype OspA and FTK-OspA peptides protect against Lyme arthritis.
Figure 5B:
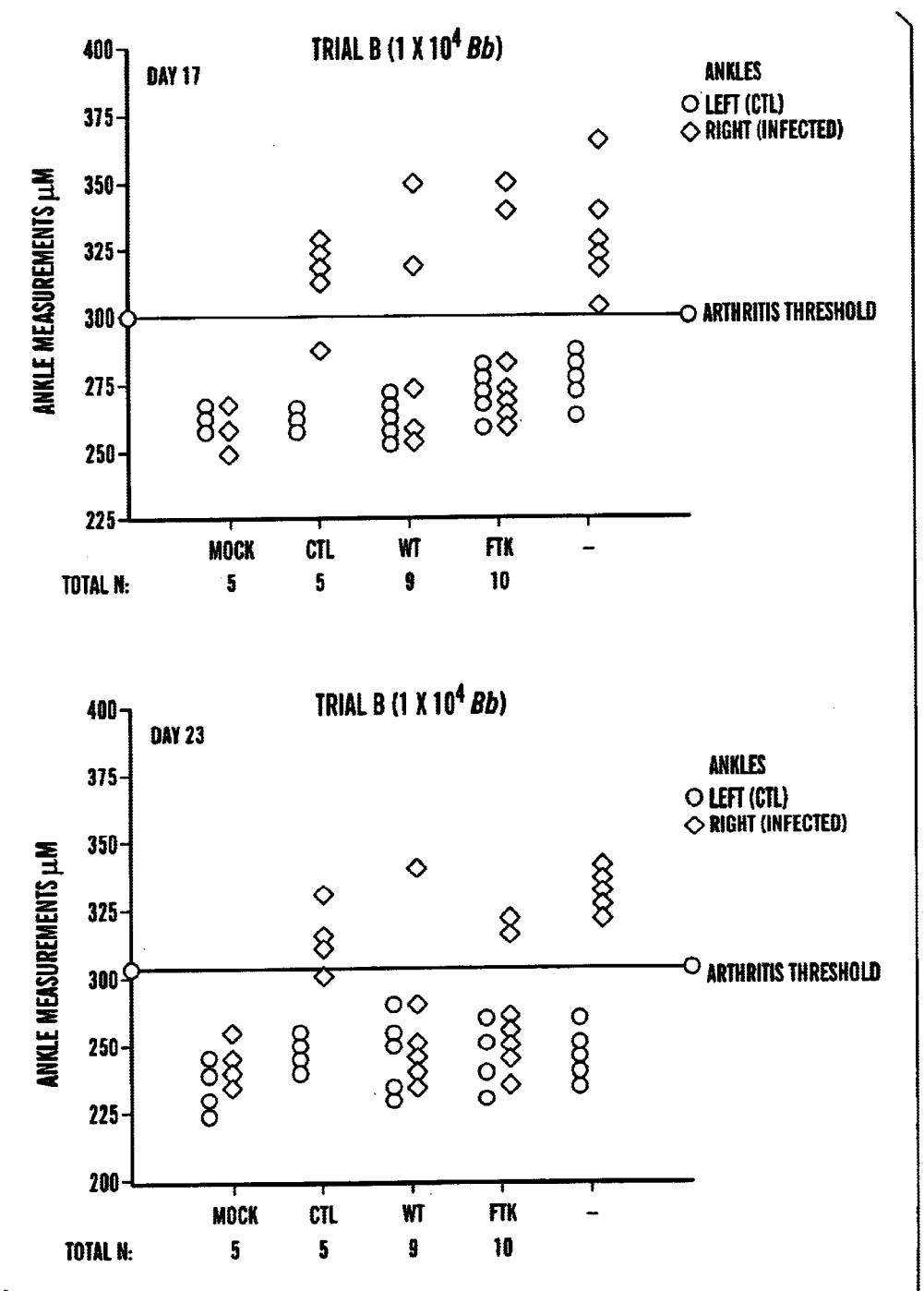

Wildtype OspA and FTK-OspA peptides protect against Lyme arthritis (FIG. 5). In trial A, mice were infected with 5×10$^3$ *B. burgdorferi*; in trial B, mice were infected with 5×10$^3$ *B. burgdorferi*. 75% of the mice vaccinated with wildtype OspA peptide prior to infection were protected from development of arthritis; 87.5% of the mice vaccinated with FTK-OspA peptide prior to infection were protected. In contrast, none of the control-vaccinated mice were protected (i.e., they all developed arthritis).

Figure 6:
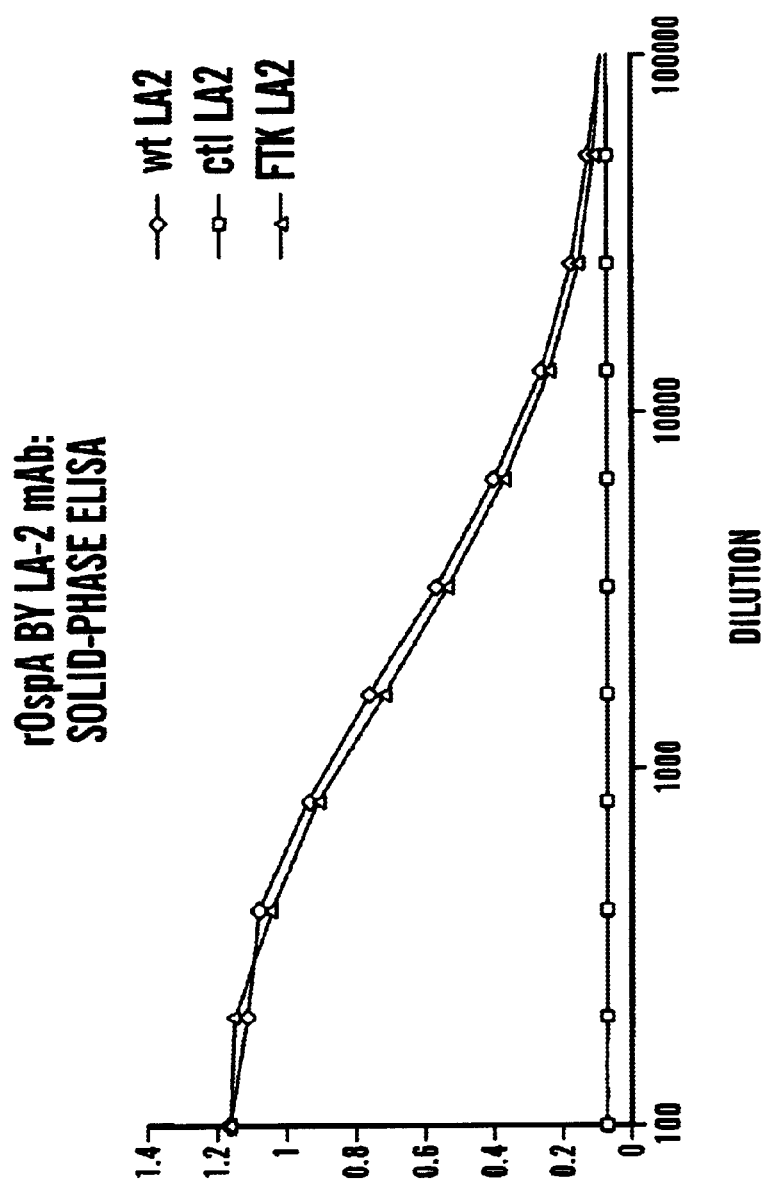
FIG. 6 shows that the protective anti-OspA monoclonal antibody, LA-2, binds to wildtype OspA and FTK-OspA equivalently.

Monoclonal antibody LA-2, which provides passive immunity against *B. burgdorferi* in mice, binds an epitope in OspA. FIG. 6 shows that this monoclonal antibody (LA-2) binds to both wildtype OspA and FTK-OspA in an in vitro assay, but does not recognized the control vaccine. FIG. 7 shows serum OspA-specific IgG is similar for wildtype OspA and FTK-OspA immunized mice.

Taken together, these data confirm the ability of the FTK-OspA polypeptide to maintain an immunogenic structure while eliminating the host cross-reactive T cell epitopes.

The references cited herein are incorporated by reference.

We claim:

1. An isolated OspA polypeptide or unique fragment thereof comprising the amino acid sequence as set forth in SEQ ID NO:4.

2. A vaccine composition comprising the isolated OspA polypeptide of claim 1 and a pharmaceutically acceptable carrier or vehicle.

3. The vaccine composition of claim 2 further comprising an adjuvant.

* * * * *

SEQUENCE LISTING

<160> NUMBER OF SEQ ID NOS: 4

<210> SEQ ID NO 1
<211> LENGTH: 9
<212> TYPE: PRT
<213> ORGANISM: Borrelia burgdorferi

```
-continued

<400> SEQUENCE: 1

Tyr Val Leu Glu Gly Thr Leu Thr Ala
1               5

<210> SEQ ID NO 2
<211> LENGTH: 9
<212> TYPE: PRT
<213> ORGANISM: Homo sapiens

<400> SEQUENCE: 2

Tyr Val Ile Glu Gly Thr Ser Lys Gln
1               5

<210> SEQ ID NO 3
<211> LENGTH: 9
<212> TYPE: PRT
<213> ORGANISM: Borrelia afzelii

<400> SEQUENCE: 3

Phe Thr Leu Glu Gly Lys Val Ala Asn
1               5

<210> SEQ ID NO 4
<211> LENGTH: 9
<212> TYPE: PRT
<213> ORGANISM: Artificial Sequence
<220> FEATURE:
<223> OTHER INFORMATION: Modified Borrelia Burgdorferi OspA

<400> SEQUENCE: 4

Phe Thr Leu Glu Gly Lys Leu Thr Ala
1               5
```